United States Patent [19]

Weinstein

[11] Patent Number: 4,626,245
[45] Date of Patent: Dec. 2, 1986

[54] HEMOSTATIS VALVE COMPRISING AN ELASTOMERIC PARTITION HAVING OPPOSED INTERSECTING SLITS

[75] Inventor: Lawrence A. Weinstein, Miami Lakes, Fla.

[73] Assignee: Cordis Corporation, Miami, Fla.

[21] Appl. No.: 771,299

[22] Filed: Aug. 30, 1985

[51] Int. Cl.⁴ .................................................. A61M 25/00
[52] U.S. Cl. ........................................ 604/167; 604/256; 137/849; 251/149.1
[58] Field of Search ............... 604/167, 169, 247, 256, 604/237; 251/149.1; 137/849

[56] References Cited

U.S. PATENT DOCUMENTS

| | | | |
|---|---|---|---|
| 2,023,267 | 12/1935 | Rapt et al. | 128/202.15 |
| 3,067,425 | 12/1962 | Colley | 128/202.15 X |
| 4,424,833 | 1/1984 | Spector et al. | 604/167 X |
| 4,430,081 | 2/1984 | Timmermans | 604/256 |

Primary Examiner—Dalton L. Truluck
Attorney, Agent, or Firm—George H. Gerstman

[57] ABSTRACT

A hemostasis valve for a catheter or the like may be a self-sealing, penetrable barrier which comprises an elastomeric partition made of an integral piece. A first slit is cut on the first side of the partition, while a second slit is cut in a second, opposite side of the partition. The first and second slits are in intersecting relation to each other, each slit having a depth sufficient to permit physical interaction with each other but insufficient to extend through the entire thickness of the partition.

7 Claims, 7 Drawing Figures

HEMOSTATIS VALVE COMPRISING AN ELASTOMERIC PARTITION HAVING OPPOSED INTERSECTING SLITS

BACKGROUND OF THE INVENTION

Hemostasis valves are currently used on catheters for performing percutaneous transluminal coronary angioplasty (PTCA), as well as angiographic procedures, for example where x-ray contrast fluid is inserted into the coronary artery.

To prevent the leakage of blood out of ends of known dilitation and guidance catheters, a hemostasis valve is provided at the proximal end of each of them, to prevent seepage of blood between the guide wire and the dilitation catheter and also between the two catheters. For example, currently, numerous types of hemostasis valves are known. See for example Stevens, U.S. Pat. No. 4,000,739.

Hemostasis valves may also be employed for the introduction of other catheters into the circulatory system in a leak proof manner. The valve may be carried by any catheter or sheath introducer which communicates with the circulatory system of the body. Another inner catheter may then be placed through the hemostasis valve, which forms a leak proof seal and a port for entry of the second catheter.

There is a need for improvement of the hemostasis valve, so that an individual valve is capable of accommodating a wider range of catheters, probe wires or the like of varying diameter, to provide increased flexibility to the physician in treating the patient. At the same time, leakage of fluids under the conditions of use must be prevented.

In accordance with this invention, a self-sealing, penetrable barrier is provided, typically for use as a hemostasis valve, which exhibits greater tolerance of varying diameter of catheters or other objects penetrating it without leakage or damage to the valve. At the same time the structure is simple, inexpensive, and manufactured with relative ease.

DESCRIPTION OF THE INVENTION

In this invention, a self-sealing, penetrable barrier is provided which comprises an elastomeric partition made of an integral piece. A first slit is cut in a first side of said partition, with a second slit being cut in a second, opposite side of the partition. The first and second slits are in intersecting relation to each other, each slit having a depth sufficient to permit physical intersection with each other, but insufficient to extend through the entire thickness of the partition.

Accordingly, access through the elastomeric partition without tearing is available only at the points of intersection of the first and second slits. There, one may advance a guide wire or a catheter through the penetrable, elastomeric partition, since at the intersection point between the first and second slits there is a closed hole extending through the partition. The partition stretches to accommodate a relatively wide range of catheter or guide wire diameters. Also, certain slit configurations as described below can provide beneficial, off-centered pulling and tugging of the elastomeric partition material as the guide wire or catheter advances through it, to provide an improvement in the seal of the guide wire or catheter.

Preferably, the elastomeric material used is a medically compatible, high-elongation material which reseals well, for example natural rubber latex, or any other appropriate elastomeric material.

The first and second slits may each define a pair of straight slit portions joined together at one end and forming a typically obtuse angle. The first and second slits may, in this way, each define an arrow configuration. Preferably, the two arrow configurations of the first and second slits point in opposed directions from each other, with the first and second slits intersecting at two separate locations. Thus it becomes possible to make penetration through the barrier at two different locations without tearing.

Preferably, the first and second slits each define a Y-shape, having a pair of angled arms and a leg. The respective legs of the first and second slits preferably point in substantially opposite directions, with each arm of each slit intersecting an arm of the other slit. The leg of the Y-shaped slit provides improvement in the behavior of the elastomeric partition, as a catheter or guide wire is advanced through it, to provide improved, more reliable sealing over other slit designs. At the same time, the force required for penetrating the elastomeric partition may be reduced.

Typically, the elastomeric partition which comprises the penetrable barrier is carried within a housing. The housing, in turn, may be positioned on the end of a catheter for medical use, although other uses of the hemostasis valve are contemplated to be within the scope of this invention.

The housing may include a typically resilient end cap which encloses the elastomeric partition in the housing, which partition is typically a rubber disk. The end cap defines an aperture for access to the disk, which aperture may be of slightly smaller diameter than the object intended to penetrate it and the disk. Thus the end cap provides a second sealing site, for a double sealing hemostasis valve which exhibits improved sealing characteristics and a greater tolerance for diameter variations of objets which penetrate it.

It is contemplated that other configurations of the hemostasis valve of this invention may be utilized, being characterized by first and second slits on opposed sides on an elastomeric partition which do not extend through the entire thickness of the partition, but which are in physical intersection with each other in at least one place, to permit a closed passageway to exist through the partition which may be forced open by an elongated, penetrating item such as a guide wire or a catheter.

DESCRIPTION OF SPECIFIC EMBODLMENT

Figure 1:
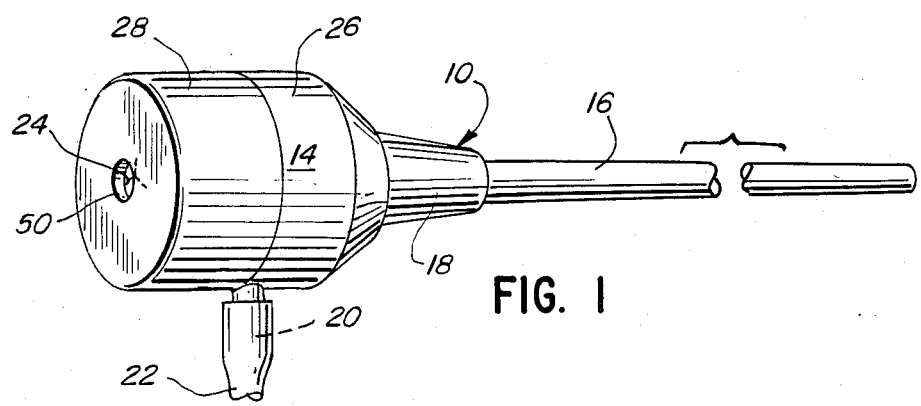
FIG. 1 is a perspective view of a catheter which carries the hemostasis valve of this invention.

Referring to the drawing, FIG. 1 shows catheter 10. Specifically, catheter 10 as shown is an outer catheter, adapted to receive an inner catheter 12 (FIG. 2) for inserting into the vascular system of a patient. Catheter 10 may be otherwise known as a "catheter sheath introducer", being used to prevent blood backflow during procedures in which a catheter is inserted or removed. Current designs of catheter sheath introducers are typically limited to a narrow range of only one or two French sizes of inner catheter 12 for which they can provide effective entry and sealing, while permitting inner catheter 12 to remain lubricious by not removing too much lubricant from it.

Outer catheter 10 defines hollow tubular housing 14 which carries catheter extension 16 positioned in attached, telescoping relation with tubular protusion 18 of the housing. Side port 20 may be of conventional design, being adapted for telescoping connection with plastic tubing 22, for providing a saline solution for flushing the interior of housing 14 and tubing extension 16.

Housing 14 also carries self-sealing, penetrable barrier 24, which may be made of an appropriate elastomeric material. For example, natural rubber latex is well-known for providing excellent resealing characteristics. However, silicone elastomeric fluoropolymers, polyurethane elastomers, or any other elastomeric material may be used, depending upon the performance parameters desired.

Figure 2:
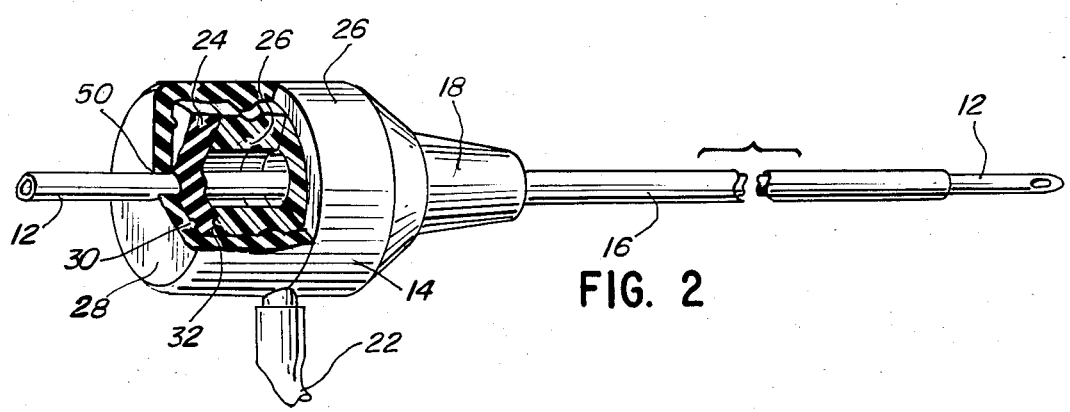
FIG. 2 is a perspective view, with a portion broken away, of the catheter and valve of FIG. 1.

Housing 14 may comprise casing portions 26, 28 which are sealed together in telescopic relation and which capture penetrable barrier 24 between them as shown in FIG. 2. Annular ribs 30, 32 may be provided in each housing portion to provide more positive capture of the elastomeric portion 24.

Figure 3:
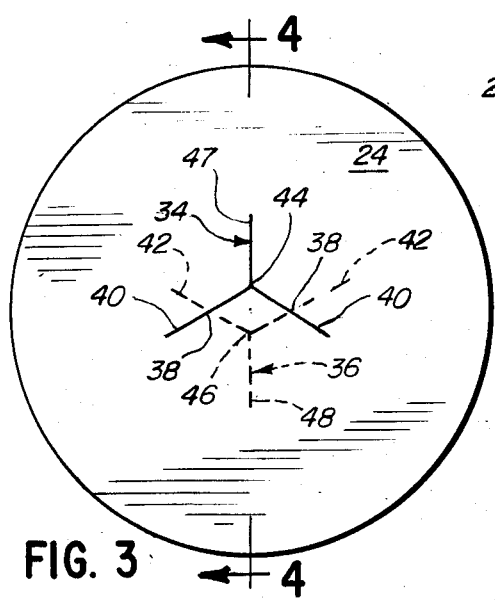
FIG. 3 is an elevational view of the elastomeric partition used in the valve carried on the catheter of FIG. 1.
Figure 4A:
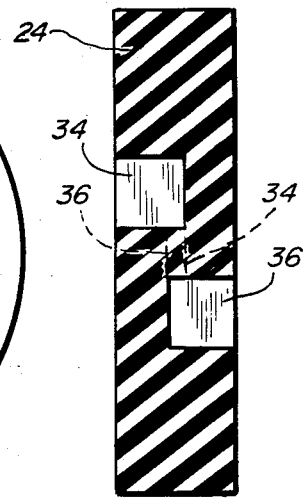
FIG. 4a and 4b are sectional views taken along line 4—4 of FIG. 3, with FIG. 4b showing an inner catheter penetrating the elastomeric barrier.
Figure 4B:
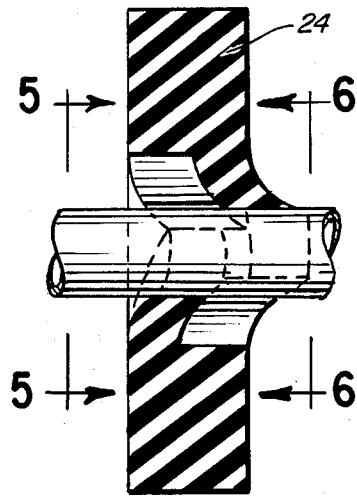

In FIGS. 3 and 4A, first slit 34 is shown in partition 24, being formed on the first side thereof, while second slit 36 is shown on the other side. Each slit 34 and 36 is shown to be Y-shaped configuration, and extends incompletely through partition 24, but is of a depth of more than half the thickness thereof. Therefore, the two slits 34, 36 overlap at intersection points 38 to form a closed channel extending completely through partition 24.

First and second slits 34, 36 each define a pair of straight slit arms 40, 42, joined together at one end 44, 46 and forming an obtuse angle as shown. Thus they each define an arrow pointing in an opposed direction from each other and also define a pair of intersection points 38.

As shown in FIG. 3, the actual shape of first and second slits 34, 36 is a Y-shape. Added to each pair of arms 40, 42 is a respective slit leg 47, 48. Preferably the respective arms and legs of the slits are all of the same depth as shown.

It can thus be seen that the path of penetration of a catheter or probe wire through elastomeric partition 24 will be made in an off-center manner. The only route of penetration through partition 24 requires traversing one of points 38. It has been found that the V-shaped arrangement of arms 40, 42, and especially the Y-shaped slit arrangement, provides improved movement and controlled stretching of the rubber material of partition 24 as the penetrating object advances, for better sealing. Additionally, the structure of this invention provides greater tolerance with respect to the diameter of objects passing through partition 24. Accordingly, a larger tolerance of diameter variation in the French sizes of catheters used, or diameters of probe wires, is exhibited by the hemostasis valve of this invention.

It is preferred for at least housing portion 28, and optionally the entire housing 14, to be resilient. Aperture 50 is provided in the outer end of housing portion 28 to provide access of catheter 12 of the like to partition 24. If access port 50 is sized to be slightly smaller than the diameter of catheter 12, when housing portion 28 is respectively resilient, a second annular seal area may be provided against catheter 12 for added sealing, this seal being a typical annular pressure seal.

Figure 5:
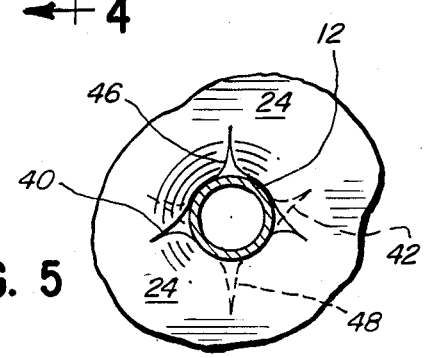
FIG. 5 is a view taken along line 5—5 of FIG. 4b.
Figure 6:
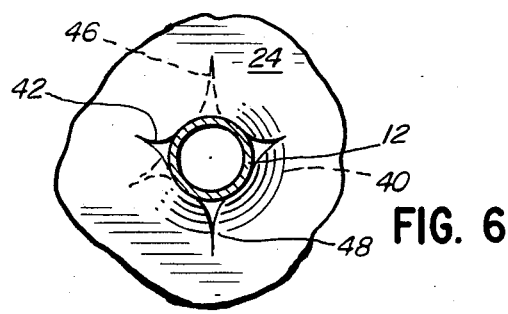
FIG. 6 is a view taken along line 6—6 of FIG. 4b.

Accordingly, a hemostasis valve is provided having improved sealing properties against a wider variety of varying diameter elongated objects for penetration thereof. It can be seen how the respective slit portions, even when stretched as in FIGS. 5 and 6, are separated by overlapping portions of the material of partition 24, which provides sealing barriers within the partition for preventing leakage about catheter 12 or any other appropriate, elongated member thrust therethrough.

The above has been offered for illustrative purposes only, and is not intended to limit the scope of the invention of this application, which is as defined in the claims below.

That which is claimed is:

1. In a hemostatic catheter including a housing mounted on the catheter, said housing including a self-sealing penetrable barrier, the improvement comprising
   an elastomeric partition valve made of one-piece construction;
   said partition valve including first slit means defined by a first side of said valve;
   second slit means defined by the opposite side of said partition valve;
   each slit means having a location which creates two spaced apart points of intersection with the other slit means;
   each slit means having a depth that is insufficient to extend through the entire thickness of said partition valve,
   whereby sealing is provided to an implement inserted through said partition valve.

2. In a hemostatic catheter as described in claim 1, wherein each of said first slit means and said second slit mens define a pair of straight slit portions joined together at one end and forming an obtuse angle.

3. In a hemostatic catheter as described in claim 1, in which each of said first slit means and said second slit means define a Y-shape having a pair of angled arms and a leg, the respective legs of said first slit means and said second slit means pointing in substantially opposite directions.

4. In a hemostatic catheter as described in claim 1, in which said elastomeric partition valve comprises a rubber disc.

5. In a hemostatic catheter as described in claim 1, in which said housing includes and end cap which encloses said elastomeric partition valve in the housing, said end cap defining and aperture for access to said elastomeric partition valve.

6. In a hemostatic catheter as described in claim 5, said aperture being of smaller diameter than the object intended to penetrate both it and said disc, and with said housing being resilient.

7. In a hemostatic catheter including a housing mounted on the catheter, said housing including a self-sealing penetrable barrier, the improvement comprising
   an elastomeric partition valve in the form of a disc, made of one piece construction;

said partition valve including first slit means defined by a first side of said valve, said first slit means defining a Y-shape having a pair of angled arms and a leg;

second slit means defind by the opposite side of said partition valve, said second slit means defining a Y-shape having a pair of angled arms and a leg;

the respective legs of said first slit means and said second slit means pointing in substantially opposite directions, with each arm of each slit intersecting an arm of the other slit whereby two spaced apart points of intersection are created; and each slit means having a depth that is insufficient to extend through the entire thickness of said partition valve.

* * * * *